(12) United States Patent
Morrison et al.

(10) Patent No.: US 10,196,524 B2
(45) Date of Patent: Feb. 5, 2019

(54) DUSTLESS POWDER MATERIALS

(75) Inventors: David M. Morrison, Plainfield, CT (US); Pierre S. Alusta, Brooklyn, CT (US); William Zavadoski, Madison, CT (US); Shigeru Kishida, Storrs, CT (US); Yoshiaki Kawasaki, Woodstock, CT (US)

(73) Assignee: MIYOSHI AMERICA, INC., Dayville, CT (US)

( * ) Notice: Subject to any disclaimer, the term of this patent is extended or adjusted under 35 U.S.C. 154(b) by 2523 days.

(21) Appl. No.: 11/142,468

(22) Filed: Jun. 2, 2005

(65) Prior Publication Data
US 2006/0286048 A1 Dec. 21, 2006

(51) Int. Cl.
| | |
|---|---|
| A61K 9/00 | (2006.01) |
| B05D 7/00 | (2006.01) |
| C09C 3/10 | (2006.01) |
| A61K 48/00 | (2006.01) |
| A61Q 1/02 | (2006.01) |
| A61Q 19/00 | (2006.01) |
| C09C 3/00 | (2006.01) |
| C09C 3/08 | (2006.01) |
| A61Q 1/06 | (2006.01) |
| A61Q 1/10 | (2006.01) |
| A61Q 1/12 | (2006.01) |

(52) U.S. Cl.
CPC ............... *C09C 3/10* (2013.01); *A61K 48/00* (2013.01); *A61Q 1/02* (2013.01); *A61Q 19/00* (2013.01); *C09C 3/006* (2013.01); *C09C 3/08* (2013.01); *A61K 2800/412* (2013.01); *A61Q 1/06* (2013.01); *A61Q 1/10* (2013.01); *A61Q 1/12* (2013.01)

(58) Field of Classification Search
None
See application file for complete search history.

(56) References Cited

U.S. PATENT DOCUMENTS

| | | | | |
|---|---|---|---|---|
| 2,101,843 | A | * | 12/1937 | Factor et al. ............... 424/63 |
| 4,251,451 | A | * | 2/1981 | Magee et al. ............. 554/157 |
| 4,606,914 | A | | 8/1986 | Miyoshi |
| 4,801,445 | A | * | 1/1989 | Fukui et al. ............... 424/69 |
| 4,863,800 | A | | 9/1989 | Miyoshi et al. |
| 4,875,927 | A | * | 10/1989 | Tadros ........................ 504/235 |
| 4,980,157 | A | * | 12/1990 | Mercado et al. ........... 424/69 |
| 5,505,937 | A | * | 4/1996 | Castrogiovanni et al. ... 424/64 |
| 5,589,531 | A | * | 12/1996 | Menashi et al. ........... 524/409 |
| 5,897,868 | A | | 4/1999 | Kobayashi et al. |
| 6,251,411 | B1 | * | 6/2001 | Kishida et al. ............. 424/401 |
| 6,296,860 | B1 | | 10/2001 | Hasegawa et al. |
| 6,416,766 | B1 | | 7/2002 | Kobayashi et al. |
| 6,482,411 | B1 | | 11/2002 | Ahuja et al. |
| 6,482,441 | B1 | | 11/2002 | Hasegawa et al. |
| 6,790,452 | B2 | | 9/2004 | Kishida et al. |
| 6,887,494 | B2 | | 5/2005 | Kobayashi et al. |
| 8,790,668 | B2 | * | 7/2014 | Clapp ........................ A61K 8/11 424/401 |
| 2002/0018790 | A1 | * | 2/2002 | Vatter et al. ................ 424/401 |
| 2003/0161805 | A1 | * | 8/2003 | Schlossman et al. ...... 424/70.12 |
| 2008/0299158 | A1 | * | 12/2008 | Kishida et al. ............. 424/401 |

FOREIGN PATENT DOCUMENTS

| | | |
|---|---|---|
| JP | 55-057511 A | 4/1980 |
| JP | 55057511 | 4/1980 |
| JP | 56029512 | 3/1981 |
| JP | 58-72512 A | 4/1983 |
| JP | 60-069011 A | 4/1985 |
| JP | 61-073775 A | 4/1986 |
| JP | 02152917 | 6/1990 |
| JP | 06-024939 A | 1/1994 |
| JP | 06345632 | 12/1994 |
| JP | 08059431 | 3/1996 |
| JP | 09-301827 A | 11/1997 |
| JP | 09301827 | 11/1997 |
| JP | 10-095711 A | 4/1998 |
| JP | 10-182163 A | 7/1998 |
| JP | 2001-72527 A | 3/2001 |
| JP | 2001072527 A | 3/2001 |

(Continued)

OTHER PUBLICATIONS

Eyeshadow. Focus on Style. Jan. 18, 2002. Accessed on Jun. 25, 2008. <http://www.focusonstyle.com/stylething/greeneyeshadow.htm>.*
Surface Active Agents. Dictionary of Chemistry Second Edition. Edited by D.W.A. Sharp. Copyright 1990.*
Isopar E. http://exxonmobilchemical.ides.com/en-US/ds128992/Isopar%E2%84%A2%20E.aspx?I=22455&U=1. Copyright 2011. Accessed Mar. 16, 2011.*
Isopar G. http://exxonmobilchemical.ides.com/datasheet.aspx?I=22455&CULTURE=en-US&PS=COMBO&E=128993. Copyright 2011. Accessed Mar. 10, 2011.*
Kobo Products. http://www.koboproductsinc.com/microspheres.html. Archived Aug. 29, 2003. Accessed Mar. 16, 2011.*

(Continued)

*Primary Examiner* — David J Blanchard
*Assistant Examiner* — Lori K Mattison
(74) *Attorney, Agent, or Firm* — Pillsbury Winthrop Shaw Pittman LLP

(57) ABSTRACT

This invention relates to a coated powder material containing a powder material having a surface layer that has been chemically immobilized with one or more surface-active agents and coated with an oil. The surface-active agents are present in an amount of at least about 0.1% by weight, based on the powder material; the oil is present in an amount ranging from about 0.1 to 180% by weight, based on the powder material; and the combined weight percentage of the surface-active agents and oil is at least about 4.0% by weight, based on the powder material. The oil-absorption rate of the powder material ranges from about 0.01 to about 0.70 gram of oil per gram of dry powder. The coated powder material is useful as a cosmetic.

20 Claims, 1 Drawing Sheet

(56) References Cited

FOREIGN PATENT DOCUMENTS

| JP | 2002080748 | 3/2002 |
|----|------------|--------|
| JP | 2005-002076 A | 1/2005 |
| JP | 2005002076 | 1/2005 |

OTHER PUBLICATIONS

Isononane. http://www.chemicalbook.com/ChemicalProductProperty_EN_CB5735123.htm. Copyright 2010. Accessed Mar. 17, 2011.*
Soltrol 130. http://www.cumulus-soaring.com/airpath/Compass%20Fluid%20MSDS.pdf. Published Nov. 15, 2002. Accessed Mar. 17, 2002.*
Affix. Collins English Dictionary. http://www.collinsdictionary.com/dictionary/english/affix. Published 2012.*
Adsorption.https://www.rpi.edu/dept/chem-eng/Biotech-Environ/Adsorb/adsorb.htm. Published Feb. 25, 2000.*
Japanese Laid-Open Publication No. 10-95711 (Japanese publication corresponding to U.S. Pat. No. 5,897,868).
Japanese Laid-Open Publication No. 58-72512 (corresponding to U.S. Pat. No. 4,606,914).
Japanese Laid-Open Publication No. 61-73775.
Official Action dated Jul. 9, 2014 in Japanese Application No. 2008-514871.
Notice of Reasons for Rejection Japanese Patent Application No. 2016-155503 dated Aug. 16, 2017 with full English translation.
Decision of Refusal Japanese Patent Application No. 2012-029504 dated Mar. 7, 2014 with English translation.
Notice of Reasons for Rejection Japanese Patent Application No. 2008-514871 dated Nov. 11, 2011 with English translation.
Notice of Reasons for Rejection Japanese Patent Application No. 2008-514871 dated Jul. 9, 2014 with English translation.
Notice of Final Rejection issued in Japanese Patent Application No. 2016-155503 dated Apr. 2, 2018 with English translation.

* cited by examiner

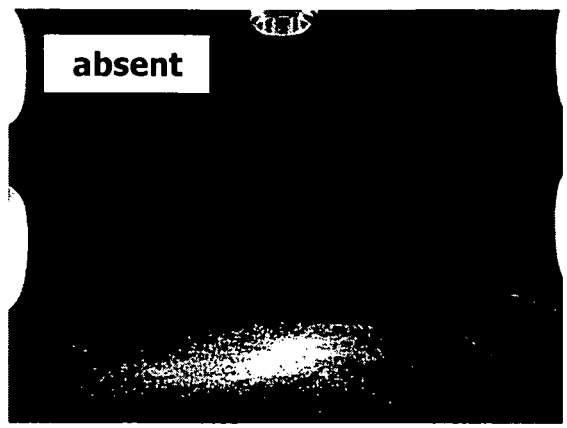
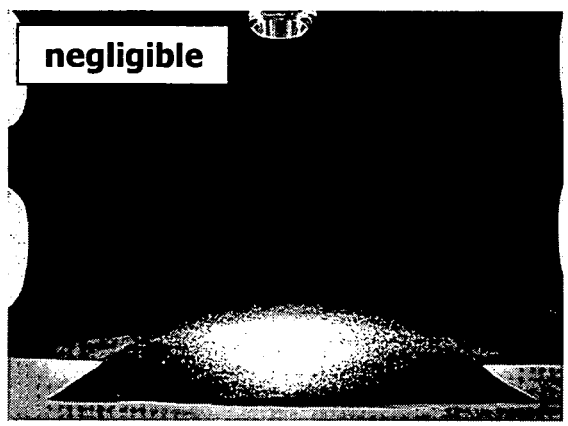
DUST GRADES

__

DUSTLESS POWDER MATERIALS

FIELD OF THE INVENTION

This invention relates to dustless powder materials, such as dustless pigments, that may be used for cosmetic products such as foundations, lip sticks, lotions, and creams.

BACKGROUND OF THE INVENTION

The preparation of pigment particles traditionally focuses on strengthening the hydrophobic properties in the pigments to improve water repellency as well as the strength and texture of the pigments. While strong hydrophobic properties are desirable for these reasons, these pigments tend to have high oil-absorption values and relatively poor dispersibility. In fact, the oil absorption of the pigments is often times so high as to require roll mills or particular mills to obtain good dispersions. Additionally, pigments with high oil-absorption values tend to create dust, which can be problematic in cosmetic production sites.

Oil-dispersed products, which are completely saturated in oil and create no dust, have been introduced to cure these problems and provide cosmetic manufacturers with ease of handling. See, for example, the Tioveil series by Uniqema. However, the high levels of pigment load, typically exceeding 55%, makes the oil dispersions exceedingly viscous and, at the same time, causes texture-stability and oil-bleeding problems.

Accordingly, what is needed in the art is a dust-free powder material that has the ability to disperse into oils and can be used in cosmetic systems without the aforementioned side effects. This invention answers that need.

BRIEF SUMMARY OF THE INVENTION

This invention relates to a coated powder material, comprising a powder material having a surface layer that has been (a) chemically immobilized with one or more surface-active agents, and (b) coated with an oil. The surface-active agents are present in an amount of at least about 0.1% by weight, based on the powder material; the oil is present in an amount ranging from about 0.1 to 180% by weight, based on the powder material; and the combined weight percentage of the surface-active agents and oil is at least about 4.0% by weigh, based on the powder material. The oil-absorption value of the powder material ranges from about 0.01 to about 0.70 gram of oil per gram of dry powder.

This invention also relates to a process for preparing a coated powder material, comprising the steps of: (a) introducing a powder material; (b) chemically immobilizing the powder material with one or more surface-active agents, and (c) coating the chemically immobilized powder material with an oil. The surface-active agents are present in an amount of at least about 0.1% by weight, based on the powder material; the oil is present in an amount ranging from about 0.1 to 180% by weight, based on the powder material; and the combined weight percentage of the surface-active agents and oil is at least about 4.0 % by weigh, based on the powder material.

BRIEF DESCRIPTION OF THE DRAWINGS

FIG. 1 illustrates three photographs taken to determine the dust grade. The photographs depict powders: (a) absent of dust, (b) having a negligible amount of dust, and (c) having a confirmed amount of dust.

DETAILED DESCRIPTION OF THE INVENTION

This invention relates to a coated powder material, comprising a powder material having a surface layer that has been (a) chemically immobilized with one or more surface-active agents, and (b) coated with an oil. The surface-active agents are present in an amount of at least about 0.1% by weight, based on the powder material; the oil is present in an amount ranging from about 0.1 to 180% by weight, based on the powder material; and the combined weight percentage of the surface-active agents and oil is at least about 4.0 % by weigh, based on the powder material. The oil-absorption value of the powder material ranges from about 0.01 to about 0.70 gram of oil per gram of dry powder. The coated powder material exhibits improved dispersibility and generates negligible or no dust when handled in its powdery form.

The term "powder material" as used herein includes organic and inorganic pigments, pigment extenders, inorganic and organic beads, metals, metal oxide powders, plastics, fillers for plastics, dehydrated dairy products, pharmaceuticals, and explosives. As known in the art, a powder is any solid, dry material consisting of extremely small, flowable particles. Any powder material known in the art that is capable of being immobilized by surface-active agents may be used, although inorganic pigments are preferred. Acceptable powder materials include, but are not limited to, titanium dioxides, zinc oxides, zirconium dioxides, iron oxides (including yellow, red, and black), ultramarines (such as ultramarine blue, ultramarine violet, etc.), manganese violet, mica (sericite), talc, chromium oxides, magnesium silicate, aluminum silicate, carbon black, cellulose, urethane, styrene, polyolefin, polyetheylene, polyamide, acrylates, calcium carbonate, zeolite, fumed silica, metal powders (such as magnesium), ceramic powders (such as silicon nitride), zirconium, starch (such as aluminum starch octenylsuccinate), pearl (such as timron super silver, a mica (and) titanium dioxide produced by Rona/EM Industries, mica (and) iron oxides (and) titanium dioxide, and titanium dioxide (and) mica (and) silica), cotton powder, aluminum/magnesium silicate beads, silica beads, nylon beads, and combinations thereof.

A paste, in contrast to powder, is a soft, viscous, speadable, non-flowable mass consisting of solid particles coated by or dispersed in a liquid. A liquid, as is well known in the art, is a smooth, frictionless substance in the fluid state of matter having no particular fixed shape (free flowing) but an invariable volume. Pastes and liquids are outside the scope of this invention.

The term "surface-active agent" encompasses all chemical agents known in the art that have the ability to affect the surface of a compound, including, but not limited to, surfactants, detergents, wetting agents, and emulsifiers. The surface-active agents need not have any special characteristics and may be nonionic or anionic, hydrophobic or hydrophilic.

Preferably, the surface-active agents have one or more reactive groups, such as a carboxyl group, a phosphorous group, a sulfur group, or a silane group. The surface-active agent may or may not contain one or more hydroxyl groups or alkylene oxide moieties, such as ethylene oxide or propylene oxide. More preferably, the surface-active agents are acyl collagens, ether carboxylic acids, lactates, gluconates, amino acids (such as thereonine and serine), acyl amino acids (such as acylglutamates, acylsarcosinates, acylglycinates, and acylalaninates), fatty acids and their salts, silanes (such as organic silane) or glycerol phosphate esters (such as lecithin). Particularly preferred surface-active agents include silane, methicone, galacturonic acid, glucarolactone, gallic acid, glucoheptanoic acid, 12-hydroxystearic acid, laurylamidobetaine, stearyl amphoacetate, lauryl amphopropionate, stearyl amphopropionate, polyethylene, sodium myristoyl sarosinate, disodium stearoyl glutamate, isostearyl sebacic acid, and combinations thereof.

The surface-active agents are chemically immobilized onto the surface of the powder material by the methods known in the art, such as those described in U.S. Pat. No. 5,897,868, herein incorporated by reference in its entirety. Chemical immobilization differs from adding the surface-active agents to the powder material in that the treated powder material has a uniformly chemically bound reaction product. The reaction may be created by a water soluble compound having a lipophilic or hydrophilic moiety being absorbed onto the surface of the powder material. With the addition of, e.g., a water-soluble salt of a polyvalent metal, a chemical bonding can be produced. The reaction product provides a chemically immobilized treatment onto the surface of the particles of the powder material. In contrast, coating a powder material with a surface-active agent only involves absorbing the surface-active agent onto the surface of the powder material. Coating of the surface of a powder material with a surface-active agent, while beneficial for other purposes, will render the surface free-flowing, unreliable, and inadequate as a functional layer.

The surface-active agents are present in an amount of at least 0.1% by weight, based on the weight of the powder material. Preferably, the surface-active agents are present in an amount ranging from about 1.0 to about 200% by weight; more preferably, from about 1.0 to about 60% by weight; and most preferably, from about 3.0 to about 30% by weight.

The oil may be any oil known in the art, including esters such as synthetic glycerides (such as monoglycerides, diglycerides, and triglycerides), fatty acid esters, hydroxyl acid esters, dimer acid esters, naturally derived esters (such as castor oil derivatives and vegetable-based oils), hydrocarbons, silicones and their derivatives (such as cyclomethicone, polysilicone-11, etc.), lipophilic vitamins, lipophilic dyes, essential oils, and combinations thereof. While oils such as dimethyl polysiloxane, dimethicone (available as DC 200 from Dow Corning), mineral oil, isostearyl neopentanoate, and caprylic/capric triglyceride have been shown to produce good results, the preference when choosing a particular oil is often dependent on the cosmetic product being produced. Generally, the oil has a viscosity ranging from 5 to 100,000 cst.

The surface layer of the powder material may be coated with the oil by any means known in the art. Preferably, the oil is applied as a liquid. Oils that are not commercially available as liquids, such as ascorbyl palmitate, which is lipophilic vitamin and sold primarily as a solid, can be solubilized in liquid oil before being used as a coating oil. Suitable solubilizing oils include vitamin acetate, caprylic/capric triglyceride, and others known in the art. Once in a liquid form, the oil may then be coated to the powder material using conventional techniques. For example, the oil may be poured into the reaction through, e.g. a reaction valve, and mixed until the composition is homogeneous.

The oil is present in an amount ranging from about 0.1 to 180% by weight, based on the weight of the powder material. Preferably, the oil is present in an amount ranging from about 1.0 to about 150% by weight; more preferably, from about 3.0 to about 120% by weight; and most preferably, from about 5.0 to about 60% by weight.

The combined weight percentage of the surface-active agents and oil is at least 4.0% by weight, based on the weight of the powder material. Preferably, the combined weight percentage ranges from 4.0 to about 300%; more preferably, from 4.0 to about 150% by weight; and most preferably, from about 8.0 to about 90% by weight.

Oil absorption is a term that shares a close relationship to surface area and is used to measure how much oil is absorbed on the exposed surfaces of the powder particles (including any oil absorbed in the voids between the individual particles). The more oil absorbed, the higher the oil absorption value.

Oil absorption may be calculated by the following technique: (1) place approximately 5 grams of sample into a weighing dish and record the weight (I); (2) transfer the sample onto a glass plate and place the glass plate under a burette with a stand and a stopcock; (3) record the starting point (D) of the oil; (4) slowly open the stopcock to release a small amount of oil onto the sample; (5) mix the oil and sample together (rub out) using a spatula; (6) repeat steps 4 and 5 until reaching the end point; (7) record the end point (E) of oil, which corresponds to the point at which the sample contains maximum consistency. Generally, the end point of a sample may be determined by observing the point at which the sample takes on a putty-like consistency (like that of peanut butter) and the shine of the oil starts to appear when the sample is spread out. If the end point is overstepped, the dull-appearing and relatively rigid appearance of a powder changes into a shiny, slumping paste. The total time for the test should be within 15 minutes from start to end point; extended rub-out time will lower the oil-absorption value and should be avoided. Oil absorption may be calculated using the following equations: Volume oil used: $E-D=F$; % w/w oil absorption=$F \times G/I \times 100$, where D=starting point of oil; E=the end point of oil; F=volume of the oil used; G=density of the oil used; and I=actual sample weight.

Mineral oil, which is commonly used as the oil used for the oil-absorption tests, has a density of 0.85 g/mi. Other oils, such as cyclopentasiloxane, isostearyl neopentanoate, caprylic/capric triglyceride, and isononyl isononanoate may also be used.

The oil-absorption value is measured as the grams of oil per grams of dry powder. The oil-absorption value of the coated powder material should range from about 0.01 to about 0.70 gram of oil per gram of dry powder. Preferably, the oil-absorption value ranges from about 0.10 to about 0.64, more preferably from about 0.12 to about 0.46.

The coated powder materials may contain conventional emulsifiers, suspending agents, emulsion stabilizers, cosmetically acceptable materials, and other agents known in the art.

The coated powder materials may be used in cosmetic products, such as foundations, lip sticks, eye shadow, lotions, creams, concealer, blush, eyeliners, mascara, eyebrow liner, lip liner, nail polish, and sunscreen. They may also be used in toiletry products, such as deodorants, antiperspirants, and shower gels. When the coated powder materials are used in a cosmetic product or a toiletry product, other typical components used in making the cosmetic product or toiletry product can be added. For instance, lip stick will often contain various oils and waxes in addition to the coated powder materials.

The invention also relates to a process for preparing a coated powder material, comprising the steps of: (a) introducing a powder material; (b) chemically immobilizing the powder material with one or more surface-active agents, and (c) coating the chemically immobilized powder material with an oil, wherein the surface-active agents are present in an amount of at least about 0.1% by weight, based on the powder material; the oil is present in an amount ranging from about 0.1 to 180% by weight, based on the powder material; and the combined weight percentage of the surface-active agents and oil is at least about 4.0% by weigh, based on the powder material.

The following examples are intended to illustrate the invention. These examples should not be used to limit the scope of the invention, which is defined by the claims.

General Procedure of Preparing a Coated Powder Material

Powder materials are mixed with 50 to 500% (based on weight of the pigment) water and dispersed. An aqueous solution of a surface-active agent, for instance, a water-soluble alkali metal salt of a fatty acid or an acyl amino acid, is added (0.5 to 400 parts surface-active agent per 100 parts powder) to the slurry and dispersed. An oil (1 to 180 parts of oil per 100 part powder) is then introduced to the system. One to two chemical equivalents of a water-soluble salt of a polyvalent metal, such as an alkaline earth metal, aluminum, titanium, zinc, or zirconium sulfate, may be added to assist in linking the functional group of the surface-active agent to the surface of the particles of the powder material. The resultant coated, surface-modified powder material is dehydrated using a filter press and rinsed with purified or de-ionized water to remove any secondary salts, as necessary. The filter cake is further dehydrated in an oven until the filter cake reaches a temperature of 100° C. for a period of over 2 hours. After the filter cake has cooled down, it is then crushed in an atomizer to produce a workable powder.

TABLE 1

Properties of various coated powder materials

| Ex. no. | Powder material | | Surface-active agent | Surface-active agent treatment (wt %) | Oil | Oil treatment (wt %) | Appearance | Dust generation | Oil absorption (g of oil per g of dry powder) | Oil used for oil absorption test |
|---|---|---|---|---|---|---|---|---|---|---|
| 1 | Pigments | Yellow 77492 | | 0 | | 0 | powdery | confirmed | 1.01 | Mineral oil |
| 2 | | PT-Y-338073 | PE | 3 | | 0 | powdery | confirmed | 0.59 | Mineral oil |
| 3 | | SAT-Y-338073 | Silane | 3 | | 0 | powdery | confirmed | 0.54 | Mineral oil |
| 4 | | Yellow 77492 | SMS | 3 | Dimethicone | 5 | powdery | negligible | 0.46 | Mineral oil |
| 5 | | Yellow 77492 | SMS | 10 | Dimethicone | 10 | powdery | negligible | 0.35 | Mineral oil |
| 6 | | Yellow 77492 | SMS | 20 | Dimethicone | 10 | powdery | absent | 0.26 | Mineral oil |
| 7 | | Yellow 77492 | SMS | 10 | Dimethicone | 100 | powdery | absent | 0.56 | Mineral oil |
| 8 | | Yellow 77492 | SMS | 20 | Dimethicone | 220 | paste | absent | n.a. | |
| 9 | | Red 77491 | | 0 | | 0 | powdery | confirmed | 0.68 | Mineral oil |
| 10 | | SAT-R-338075 | Silane | 3 | | 0 | powdery | confirmed | 0.44 | Mineral oil |
| 11 | | PT-R-33128 | PE | 3 | | 0 | powdery | confirmed | 0.29 | Mineral oil |
| 12 | | Red 77491 | SMS | 1 | Dimethicone | 3 | powdery | negligible | 0.12 | Mineral oil |
| 13 | | Red 77491 | SMS | 3 | Dimethicone | 5 | powdery | negligible | 0.12 | Mineral oil |
| 14 | | Red 77491 | SMS | 0.5 | Dimethicone | 40 | powdery | absent | 0.30 | Mineral oil |
| 15 | | Red 77491 | SMS | 0.5 | Dimethicone | 60 | powdery | absent | 0.38 | Mineral oil |
| 16 | | Red 77491 | SMS | 1 | Dimethicone | 100 | powdery | absent | 0.50 | Mineral oil |
| 17 | | Red 77491 | SMS | 10 | Dimethicone | 190 | paste | absent | n.a. | |
| 18 | | Black 77499 | | 0 | | 0 | powdery | confirmed | 0.60 | Mineral oil |
| 19 | | PT-B-33134 | PE | 3 | | 0 | powdery | confirmed | 0.30 | Mineral oil |
| 20 | | SAT-B-335198 | Silane | 3 | | 0 | powdery | confirmed | 0.21 | Mineral oil |
| 21 | | Black 77499 | SMS | 3 | Dimethicone | 5 | powdery | negligible | 0.12 | Mineral oil |
| 22 | | Black 77499 | SMS | 5 | Dimethicone | 10 | powdery | absent | 0.13 | Mineral oil |
| 23 | | Black 77499 | SMS | 5 | Dimethicone | 25 | powdery | absent | 0.19 | Mineral oil |
| 24 | | Black 77499 | SMS | 10 | Dimethicone | 215 | paste | absent | n.a. | |
| 25 | | TRI-77891 | | 0 | | 0 | powdery | confirmed | 0.86 | Mineral oil |
| 26 | | PT-T-47051 | PE | 3 | | 0 | powdery | confirmed | 0.30 | Mineral oil |
| 27 | | SAT-T-CR837 | Silane | 3 | | 0 | powdery | confirmed | 0.22 | Mineral oil |
| 28 | | TRI-77891 | SMS | 3 | Dimethicone | 5 | powdery | negligible | 0.12 | Mineral oil |
| 29 | | TRI-77891 | SMS | 5 | Dimethicone | 10 | powdery | negligible | 0.12 | Mineral oil |
| 30 | | TRI-77891 | SMS | 5 | Dimethicone | 30 | powdery | absent | 0.24 | Mineral oil |
| 31 | | TRI-77891 | SMS | 5 | Dimethicone | 60 | powdery | absent | 0.37 | Mineral oil |
| 32 | | TRI-77891 | SMS | 5 | Dimethicone | 120 | powdery | absent | 0.53 | Mineral oil |
| 33 | | TRI-77891 | SMS | 15 | Dimethicone | 195 | paste | absent | n.a. | |
| 34 | Ultra-fine | TTO-55A | | 0 | | 0 | powdery | confirmed | 1.00 | Mineral oil |
| 35 | TiO$_2$ | TTO-55A | SMS | 3 | Dimethicone | 5 | powdery | negligible | 0.25 | Mineral oil |
| 36 | | TTO-55A | SMS | 10 | Dimethicone | 10 | powdery | negligible | 0.20 | Mineral oil |
| 37 | | TTO-55A | SMS | 21 | Dimethicone | 10 | powdery | negligible | 0.10 | Mineral oil |
| 38 | Nano- | TTO-V3 | | 0 | | 0 | powdery | confirmed | 1.68 | Mineral oil |
| 39 | titanium | TTO-V3 | SMS | 30 | | 0 | powdery | confirmed | 0.70 | Mineral oil |
| 40 | dioxide | TTO-V3 | SMS | 30 | Dimethicone | 20 | powdery | negligible | 0.52 | Mineral oil |
| 41 | | TTO-V3 | SMS | 30 | Dimethicone | 30 | powdery | negligible | 0.46 | Mineral oil |
| 42 | | TTO-V3 | SMS | 30 | Dimethicone | 60 | powdery | absent | 0.47 | Mineral oil |
| 43 | | TTO-V3 | SMS | 30 | Dimethicone | 90 | powdery | absent | 0.46 | Mineral oil |
| 44 | | TTO-V3 | SMS | 30 | Dimethicone | 120 | powdery | absent | 0.50 | Mineral oil |
| 45 | | TTO-V3 | SMS | 60 | | 0 | powdery | confirmed | 0.67 | Mineral oil |
| 46 | | TTO-V3 | SMS | 60 | Dimethicone | 10 | powdery | negligible | 0.42 | Mineral oil |
| 47 | | TTO-V3 | SMS | 60 | Dimethicone | 150 | paste | absent | n.a. | |
| 48 | | Amorphous titanium dioxide | | 0 | | 0 | powdery | confirmed | 1.71 | Mineral oil |
| 49 | | Amorphous titanium dioxide | SMS | 200 | Dimethicone | 1 | powdery | negligible | 0.00 | Mineral oil |

TABLE 1-continued

Properties of various coated powder materials

| Ex. no. | Powder material | Surface-active agent | Surface-active agent treatment (wt %) | Oil | Oil treatment (wt %) | Appearance | Dust generation | Oil absorption (g of oil per g of dry powder) | Oil used for oil absorption test |
|---|---|---|---|---|---|---|---|---|---|
| 50 | Amorphous titanium dioxide | Silane | 400 | Dimethicone | 1 | powdery | absent | 0.00 | Mineral oil |
| 51 Inorganic beads | Aluminum/magnesium silicate | | 0 | | 0 | powdery | confirmed | 0.30 | Mineral oil |
| 52 | Aluminum/magnesium silicate | SMS | 3 | Dimethicone | 6 | powdery | negligible | 0.18 | Mineral oil |
| 53 | Aluminum/magnesium silicate | SMS | 6 | Dimethicone | 6 | powdery | negligible | 0.20 | Mineral oil |
| 54 | Aluminum/magnesium silicate | SMS | 12 | Dimethicone | 6 | powdery | negligible | 0.21 | Mineral oil |
| 55 | Aluminum/magnesium silicate | SMS | 15 | Dimethicone | 6 | powdery | negligible | 0.23 | Mineral oil |
| 56 | Aluminum/magnesium silicate | SMS | 21 | Dimethicone | 6 | powdery | absent | 0.22 | Mineral oil |
| 57 | Aluminum/magnesium silicate | SMS | 12 | Dimethicone | 50 | paste | absent | n.a. | |
| 58 Pigments | Mica | | 0 | | 0 | powdery | confirmed | 1.02 | Mineral oil |
| 59 | Mica | ISS | 3 | | 0 | powdery | confirmed | 0.35 | Mineral oil |
| 60 | Mica | ISS/SSG | 3/0.5 | | 0 | powdery | confirmed | 0.33 | Mineral oil |
| 61 | Mica | Silane | 2 | | 0 | powdery | confirmed | 0.32 | Mineral oil |
| 62 | Mica | SSG | 3 | | 0 | powdery | confirmed | 0.46 | Mineral oil |
| 63 | Mica | ISS | 3 | Mineral Oil | 3 | powdery | negligible | 0.21 | Mineral oil |
| 64 | Mica | ISS/SSG | 3/0.5 | Mineral Oil | 3 | powdery | negligible | 0.20 | Mineral oil |
| 65 | Mica | Silane | 2 | Mineral Oil | 3 | powdery | negligible | 0.20 | Mineral oil |
| 66 | Mica | SSG | 3 | Mineral Oil | 3 | powdery | negligible | 0.27 | Mineral oil |
| 67 | Mica | ISS | 3 | | 0 | powdery | confirmed | 0.40 | D5 |
| 68 | Mica | ISS/SSG | 3/0.5 | | 0 | powdery | confirmed | 0.36 | D5 |
| 69 | Mica | Silane | 2 | | 0 | powdery | confirmed | 0.30 | D5 |
| 70 | Mica | SSG | 3 | | 0 | powdery | confirmed | 0.57 | D5 |
| 71 | Mica | ISS | 3 | Dimethicone | 3 | powdery | negligible | 0.28 | D5 |
| 72 | Mica | ISS/SSG | 3/0.5 | Dimethicone | 3 | powdery | negligible | 0.24 | D5 |
| 73 | Mica | Silane | 2 | Dimethicone | 3 | powdery | negligible | 0.20 | D5 |
| 74 | Mica | SSG | 3 | Dimethicone | 3 | powdery | negligible | 0.38 | D5 |
| 75 | Mica | ISS | 3 | | 0 | powdery | confirmed | 0.38 | IS-Neo |
| 76 | Mica | ISS/SSG | 3/0.5 | | 0 | powdery | confirmed | 0.31 | IS-Neo |
| 77 | Mica | Silane | 2 | | 0 | powdery | confirmed | 0.33 | IS-Neo |
| 78 | Mica | SSG | 3 | | 0 | powdery | confirmed | 0.44 | IS-Neo |
| 79 | Mica | ISS | 3 | IS-Neo | 3 | powdery | negligible | 0.23 | IS-Neo |
| 80 | Mica | ISS/SSG | 3/0.5 | IS-Neo | 3 | powdery | negligible | 0.18 | IS-Neo |
| 81 | Mica | Silane | 2 | IS-Neo | 3 | powdery | negligible | 0.19 | IS-Neo |
| 82 | Mica | SSG | 3 | IS-Neo | 3 | powdery | negligible | 0.27 | IS-Neo |
| 83 | Mica | ISS | 3 | | 0 | powdery | confirmed | 0.37 | C8-Trigly |
| 84 | Mica | ISS/SSG | 3/0.5 | | 0 | powdery | confirmed | 0.35 | C8-Trigly |
| 85 | Mica | Silane | 2 | | 0 | powdery | confirmed | 0.38 | C8-Trigly |
| 86 | Mica | SSG | 3 | | 0 | powdery | confirmed | 0.45 | C8-Trigly |
| 87 | Mica | ISS | 3 | C8-Trigly | 3 | powdery | negligible | 0.20 | C8-Trigly |
| 88 | Mica | ISS/SSG | 3/0.5 | C8-Trigly | 3 | powdery | negligible | 0.18 | C8-Trigly |
| 90 | Mica | Silane | 2 | C8-Trigly | 3 | powdery | negligible | 0.19 | C8-Trigly |
| 91 | Mica | SSG | 3 | C8-Trigly | 3 | powdery | negligible | 0.25 | C8-Trigly |
| 92 Nano- | TTO-V3 | | 0 | | 0 | powdery | confirmed | 1.70 | Mineral oil |
| 93 titanium | TTO-V3 | SMS | 20 | Dimethicone | 15 | powdery | negligible | 0.58 | Mineral oil |
| 94 dioxide | TTO-V3 | SMS | 20 | Dimethicone | 15 | powdery | negligible | 0.55 | ININ |
| 95 | TTO-V3 | SMS | 20 | Dimethicone | 15 | powdery | negligible | 0.52 | Dimethicone |
| 96 Starch | DryFlo PC | | 0 | | 0 | powdery | confirmed | 0.37 | Mineral oil |
| 97 | DryFlo PC | SMS | 3 | Dimethicone | 10 | powdery | negligible | 0.25 | Mineral oil |
| 98 Pearl | Timron Super Silver | | 0 | | 0 | powdery | confirmed | 1.19 | Mineral oil |
| 99 | Timron Super Silver | SMS | 2 | Dimethicone | 5 | powdery | negligible | 0.64 | Mineral oil |

PE = polyethylene
SMS = sodium myristoyl sarosinate
ISS = isostearyl sebacic acid
SSG = disodium stearoyl glutamate
DryFloPC = aluminum starch octenylsuccinate (manufactured by National Starch)
TTO-V3 = titanium dioxide (nano-particle; manufactured by Ishihara Sangyo)
TTO-55A = titanium dioxide (ultrafine particle; manufactured by Ishihara Sangyo)
D5 = cyclopentasiloxane
IS-Neo = isostearyl neopentanoate
C8-Trigly = caprylic/capric triglyceride
ININ = isononyl isononanoate For appearance, the material was classified as powdery if the material contained flowable particles capable of creating an angle of repose. If the material did not contain flowable materials capable of creating an angle of repose, the material was classified as a paste or liquid, depending on the other properties exhibited.

For dust generation, the amount of dust generated by the powder material was determined through visual observation by the following method: (1) weigh out 80 grams of powder in a container; (2) position the container approximately two feet above an appropriate surface and quickly empty the contents onto the surface; (3) photograph the aftermath approximately one second after impact; and (4) evaluate the photograph to determine dust content. If an undeniable amount of dust was observed, the dust generation was considered "confirmed"; if only trace amounts of dust was observed, the dust generation was considered "negligible"; and if no dust was observed, the dust generation was considered "absent." FIG. 1 contains three photographs illustrating the three classifications of dust generation.

Examples 4-7, 12-16, 21-23, 28-32, 35-37, 40-44, 46, 52-56, 63-66, 71-74, 79-82, 87-91, 93-95, 97, and 99 are run in accordance with the invention; examples 1-3, 8-11, 17-20, 24-27, 33, 34, 38, 39, 45, 47-51, 57-62, 67-70, 75-78, 83-86, 92, 96, and 98 are comparative examples.

The coated powder materials may be used in various cosmetic and toiletry products. Set forth below are examples of a w/o liquid foundation, w/s liquid foundation, pressed powder foundation, o/w liquid foundation, loose powder, hot-pour cream foundation, mascara, eye shadow, and lip stick using the coated powder materials.

As used in these examples, the term "QS," as is accustomed in the art, stands for "sufficient quantity" to obtain the desired functionality. For a fragrance, the functionality is typically obtained using from about 0.05 to 1.0 wt %; for a preservative, the functionality is typically obtained using from about 0.01 to 1.0 wt %.

| w/o (water in oil) Liquid Foundation | | | |
|---|---|---|---|
| Part | Ingredients (INCI Name) | | % wt |
| A | Dextrin Palmitate | | 2.0 |
|   | Cyclopentasiloxane (and) PEG/PPG-18/18 | | 7.0 |
|   | Dimethicone Caprylic/Capric Triglyceride | | 5.0 |
|   | Cetyl Ethylhexanoate | | 3.0 |
| B | SMS-treated Dimethicone-coated titanium dioxide of example 35 | | 9.5 |
|   | SMS-treated Dimethicone-coated iron oxide of example 4 | | 2.4 |
|   | SMS-treated Dimethicone-coated iron oxide of example 13 | | 0.8 |
|   | SMS-treated Dimethicone-coated iron oxide of example 21 | | 0.2 |
|   | SMS-treated Dimethicone-coated nano-titanium dioxide of example 40 | | 1.5 |
|   | SMS-treated Dimethicone-coated Aluminum/magnesium silicate of example 52 | | 1.5 |
|   | Polymethylmethacrylate | | 0.5 |
|   | Isononyl Isononanoate | | 10.0 |
|   | Isodecyl Neopentanoate | | 10.0 |
|   | Cyclomethicone (and) Dimethicone Crosspolymer | | 5.0 |
|   | Ascorbyl Palmitate | | 0.3 |
|   | Tocopheryl Acetate | | 0.5 |
|   | Retinyl Palmitate | | 0.1 |
| C | D.I. Water | | Balance to 100.0 |
|   | Sodium Chloride | | 0.5 |
|   | Diglycerin | | 0.5 |
|   | Sodium Ascorbyl Phosphate | | 0.5 |
|   | Sodium Carboxymethyl Betaglucan | | 0.5 |
|   | Panthenol | | 0.5 |
|   | Zinc PCA | | 0.5 |
|   | Preservative | | QS |

Procedure:
1. Weigh the ingredients of Part A in a side container and start mixing. Start heating to about 85° C. When all the ingredients are dissolved, cool the container down to below 45° C.
2. Weigh isononyl isononanoate and cyclomethicone (and) dimethicone crosspolymer of Part B in a main container. Start homogenizer and add remaining components of Part B. Continue mixing at room temperature until homogeneous texture is obtained.
3. Transfer Part A to the container holding Part B. Continue mixing at room temperature until homogeneous texture is obtained.
4. Weigh D.I. water of Part C is a side container. Add D.I. water to the main container while mixing. Continue mixing at room temperature until everything is dissolved.
5. Add remaining components of Part C to the main component to emulsify while homogenizing at room temperature. Continue homogenization until uniform texture is obtained.

| w/s (water in silicone) Liquid Foundation | | |
|---|---|---|
| Part | Ingredients (INCI Name) | % wt |
| A | Dextrin Palmitate | 1.85 |
|   | PEG-10 Dimethicone | 1.85 |
|   | Tricaprylin | 5.00 |
| B | Cyclopentasiloxane | 20.00 |
| C | SMS-treated Dimethicone-coated titanium dioxide of example 35 | 9.5 |
|   | SMS-treated Dimethicone-coated iron oxide of example 4 | 2.4 |
|   | SMS-treated Dimethicone-coated iron oxide of example 13 | 0.8 |
|   | SMS-treated Dimethicone-coated iron oxide of example 21 | 0.2 |
|   | SMS-treated Dimethicone-coated nano-titanium dioxide of example 40 | 1.5 |
|   | SMS-treated Dimethicone-coated Aluminum/magnesium silicate of example 52 | 1.0 |
|   | Talc (and) Dimethicone | 1.65 |
| D | D.I. Water | Balance to 100.00 |
|   | Sodium Chloride | 0.50 |
|   | Pentylene glycol | 1.00 |
|   | Magnesium Ascorbyl Phosphate | 0.50 |
|   | Potassium Glycyrrhizinate | 0.50 |
|   | Pyridoxine Hydrochloride | 0.50 |
|   | Preservative | QS |

Procedure:
1. Weigh the components of Part A in a side container and start mixing. Heat to about 85° C. When all the ingredients are dissolved, cool down to about 70° C.
2. At about 70° C., add the components of Part B to the batch and mix well. Continue cooling down to about 40-50° C.
3. Blend the components of Part C in a blender. Add the blended components to the batch and homogenize.
4. Slowly add the components of Part D to the batch at about 40-50° C. while homogenizing. Cool down to room temperature.

| Pressed Powder Foundation | | |
|---|---|---|
| Part | Ingredients (INCI Name) | % wt |
| A | SMS-treated Dimethicone-coated titanium dioxide of example 35 | 15.0 |
|   | SMS-treated Dimethicone-coated iron oxide of example 4 | 3.0 |
|   | SMS-treated Dimethicone-coated iron oxide of example 13 | 1.0 |
|   | SMS-treated Dimethicone-coated iron oxide of example 21 | 0.2 |
|   | Surface-treated talc (regular surface treatment; SA-type treatment) | 20.0 |
|   | SSG-treated Dimethicone-coated (3/3) mica of example 74 | 35.0 |

| Pressed Powder Foundation | | |
|---|---|---|
| Part | Ingredients (INCI Name) | % wt |
| | SMS-treated Dimethicone-coated nano-titanium dioxide of example 40 | 10.0 |
| | Methyl Methacrylate Crosspolymer | 2.0 |
| | SMS-treated Dimethicone-coated Aluminum/magnesium silicate of example 52 | 2.0 |
| | Nylon-12 | 4.0 |
| B | Squalene | 2.0 |
| | Octyldodecyl Myristate | 1.0 |
| | Diisooctanoic Neopentanoate | 1.0 |
| | Acetylated Lanolin | 0.5 |
| | Sorbitan Oleate | 0.5 |
| | Panthotenic Alcohol | 0.5 |
| | Ascorbyl Palmitate | 0.1 |
| | Tocopheryl Acetate | 0.2 |
| | Retinyl Palmitate | 0.05 |
| C | Preservative | QS |
| | Fragrance | QS |

Procedure:
1. Blend the components of Part A in a main container and start mixing.
2. Weigh the components of Part B in a side container and mix well. When the components of Part B becomes uniform, add to the main container. Continue mixing the main container at room temperature until the components becomes wet homogeneously.
3. Add the components of Part C to the batch.
4. Measure the composition in a weighing boat and fill pan. Apply certain pressure through the powder press machine to form the pressed powder foundation.

| o/w (oil in water) Liquid Foundation | | |
|---|---|---|
| Part | Ingredients (INCI Name) | % wt |
| A | Glyceryl Stearate (and) PEG-100 Stearate | 5.00 |
| | Steareth-2 | 0.5 |
| | Beheneth-25 | 1.00 |
| | Ethylhexyl Palmitate | 2.00 |
| | Isononyl Isononanoate | 2.00 |
| | Dicaprylyl Carbonate | 5.00 |
| | Ascorbyl Tocopheryl Maleate | 1.00 |
| B | SMS-treated, Dimethicone-coated titanium dioxide of example 35 | 5.00 |
| | SMS-treated, Dimethicone-coated iron oxide of example 4 | 3.00 |
| | SMS-treated, Dimethicone-coated iron oxide of example 13 | 1.00 |
| | SMS-treated, Dimethicone-coated iron oxide of example 21 | 0.30 |
| | SMS-treated, Dimethicone-coated aluminum Starch Octenylsuccinate of example 97 | 2.00 |
| | SMS-treated Dimethicone-coated nano-titanium dioxide of example 40 | 5.00 |
| C | Cyclomethicone | 8.00 |
| | Dimethicone Copolyol | 1.00 |
| D | D.I. Water | Balance to 100.00 |
| | Hectorite | 0.30 |
| | Xanthan Gum | 0.30 |
| | Magnesium Aluminum Silicate | 0.60 |
| | Potassium Glycyrrhizinate | 0.50 |
| | Butylene glycol | 1.00 |
| | Preservative | QS |

Procedure:
1. Weigh the components of Part A in a side container and heat to about 80° C. while mixing.
2. Weigh the components of Part B in a side container and blend using a blender.
3. Add the components of Part B to Part A and mix well until a homogeneous dispersion is obtained. Cool down to below 65° C.
4. Add the components of Part C to the side container containing Parts A and B and mix well.
5. Add the components of Part D to a main container and heat to about 60-65° C.
6. Add the components in the side container (Parts A-C) to the main container (containing Part D) and homogenize at about 65° C. for an extended period of time. Cool down to room temperature while mixing.

| Loose Powder | | |
|---|---|---|
| Part | Ingredients (INCI Name) | % wt |
| A | SMS-treated Dimethicone-coated iron oxide of example 4 | 0.75 |
| | SMS-treated Dimethicone-coated iron oxide of example 13 | 0.25 |
| | SMS-treated Dimethicone-coated iron oxide of example 21 | 0.05 |
| | SMS-treated Dimethicone-coated aluminum/magnesium silicate of example 52 | 2.00 |
| | SSG-treated Dimethicone-coated (3/3) mica of example 74 | 3.00 |
| B | Ethylhexyl Palmitate | 4.00 |
| | Preservative | QS |
| | Fragrance | QS |
| C | SSG-treated Dimethicone-coated (3/3) mica of example 74 | 15.0 |
| | Surface-treated talc (regular surface treatment; SA-type treatment) | Balance to 100.0 |

Procedure:
1. Blend the components of Part A using a blender.
2. Weigh the components of Part B in a side container and mix well. When the components of Part B becomes uniform, add to the blender. Continue mixing at room temperature until the components becomes wet homogeneously.
3. Add the components of Part C to the blender while mixing. Continue mixing until the texture becomes uniform. Fill the composition in containers.

| Hot-Pour Cream Foundation (Anhydrous) | | |
|---|---|---|
| Part | Ingredients (INCI Name) | % wt |
| A | Polyglyceryl-2-triisostearate | 12.00 |
| | Diisostearyl Malate | 8.00 |
| | Dimethicone | 14.50 |
| | Cholesterol Hydroxystearate | 1.50 |
| | Tocopheryl Acetate | 0.10 |
| | Candellila Wax | 3.20 |
| | Ceresin | 3.20 |
| | Butylparaben | 0.20 |
| | Propylparaben | 0.10 |
| B | Neopentyl Glycol Dicaprate | 10.00 |
| | Isooctyl Isononanoate | 8.50 |
| | Dextrin Palmitate | 3.00 |
| C | SMS-treated Dimethicone-coated iron oxide of example 4 | 3.00 |
| | SMS-treated Dimethicone-coated iron oxide of example 13 | 1.00 |
| | SMS-treated Dimethicone-coated iron oxide of example 21 | 0.03 |
| | SMS-treated Dimethicone-coated titanium dioxide of example 35 | 2.00 |
| | SSG-treated Dimethicone-coated (3/3) mica of example 74 | 3.00 |
| | Methyl Methacrylate Crosspolymer | 5.00 |
| | Mica (and) Silica (and) Dimethicone | 3.00 |

Procedure:
1. Heat the components of Part A to about 80-85° C. in a side container and mix well until uniform.
2. Heat the components of Part B to about 80-85° C. in a separate side container and mix well until uniform.
3. Add the components of Part B to Part A and mix well.
4. Blend the components of Part C using a blender and add the blended components to the batch at about 80-85° C. while homogenizing.
5. Fill the product into pan while keeping the temperature at about 80-85° C. Allow to cool.

| Mascara | | |
|---|---|---|
| Part | Ingredients (INCI Name) | % wt |
| A | Carnauba Wax | 1.00 |
| | Candellila Wax | 5.00 |
| | Bees Wax | 5.00 |
| | Ozokerite Wax | 2.00 |
| | Stearic Acid | 5.00 |

Mascara

| Part | Ingredients (INCI Name) | % wt |
|---|---|---|
| | Cetyl Alcohol | 3.00 |
| | Shea Butter | 3.00 |
| B | SMS-treated Dimethicone-coated iron oxide of example 21 | 12.00 |
| C | Deionized Water | Balance to 100.00 |
| | Propylene Glycol | 3.00 |
| | Acrylates/Octylacrylamide Copolymer | 5.00 |
| | Sodium Hydroxide | 0.80 |
| D | Propylene Glycol (and) Diazolidinyl Urea (and) Methylparaben (and) Propylparaben | 1.00 |

Procedure:
1. Heat the components of Part A to about 80-85° C. and mix well until uniform.
2. Heat the components of Part B to about 80-85° C. and mix well until uniform.
3. Add the components of Part C together and heat to about 80-85° C.
4. Add Parts A, B, and C to a propeller mixer and mix at room temperature until the composition becomes wet homogeneously.
5. Cool down while mixing. At about 45-50° C., add Part D into the batch. Continue mixing and cooling to room temperature.

Eye Shadow

| Part | Ingredients (INCI Name) | % wt |
|---|---|---|
| A | Talc | Balance to 100.0 |
| | Magnesium Stearate | 6.00 |
| B | SMS-treated Dimethicone-coated (2/5) pearl of example 99 | 30.00 |
| C | SSG-treated Dimethicone-coated (3/3) mica of example 74 | 3.00 |
| | SMS-treated Dimethicone-coated Aluminum/magnesium silicate of example 52 | 13.00 |
| | SMS-treated Dimethicone-coated Aluminum Starch Octenylsuccinate of example 97 | 13.00 |
| D | Isopropyl Palmitate | 10.00 |
| | Cetyl Palmitate | 1.00 |
| | Preservatives | QS |

Procedure:
1. Blend the components of Part A using a blender.
2. Weigh the components of Part D in a side container and mix well.
3. Add the components of Part D to the blender while blending.
4. Pulverize the resulting composition with a 0.27-mm screen twice.
5. Blend the components of Part B and Part C with a blender.
6. Mix blended components of Parts B and C with pulverized mix of Parts A and D well until a uniform texture is obtained.
7. Press into pans.

Lipstick

| Part | Ingredients (INCI Name) | % wt |
|---|---|---|
| A | Castor Oil | 30.00 |
| | Candellila Wax | 5.50 |
| | Carnauba Wax | 2.00 |
| | Ozokerite Wax | 1.50 |
| | Microcrystalline Wax | 2.00 |
| | Caprylic/Capric Triglyceride | 15.00 |
| | Hydrogenated Castor Oil Dimer Dilinoleate | 7.50 |
| | Octyldodecyl Stearoyl Stearate | 6.00 |
| | Preservatives | QS |
| B | Castor Oil | 7.00 |
| | Organic Pigments | 3.00 |
| C | SMS-treated Dimethicone-coated (2/5) pearl of example 99 | 20.00 |
| | SMS-treated Dimethicone-coated aluminum/magnesium silicate of example 53 | 2.00 |

Procedure:
1. Blend the components of Part B using a roller mill until dispersed.
2. Heat the components of Part A at about 85-90° C. until the components have melt and become clear.
3. Add the components of Part B to Part A while heating at about 85-90° C. Mix well until uniform.
4. Add the components of Part C to the batch and continue mixing until a uniform texture is obtained.
5. Fill into mold and cool down to room temperature.

W/O sunscreen

| Part | Ingredients (INCI Name) | % wt |
|---|---|---|
| A | Polyglyceryl-4 Isosstearate (and) Cetyl PEG/PPG-10/1 Dimethicone (and) Hexyl Laurate | 5.00 |
| | Isononyl Isononanoate | 5.00 |
| | Isodecyl Neopentanoate | 3.00 |
| | Hydroxyethylacrylate/Sodium Acryloymethyltaurate Copolymer (and) Squalane (and) Polysorbate 60 | 3.00 |
| | SMS-treated Dimethicone-coated nano-titanium dioxide of example 41 | 15.00 |
| | Cyclomethicone | 14.00 |
| | Tocopheryl Acetate | 0.50 |
| | Retinyl Palmitate | 0.10 |
| | Bisabolol | 0.10 |
| | Fragrance | QS |
| B | Deionized Water | Balance to 100.00 |
| | Sodium Chloride | 0.50 |
| | Butylene Glycol | 2.00 |
| | Disodium EDTA | QS |
| | Dipotassium Glycyrrhizate | 0.10 |
| | Sodium Ascorbyl Phosphate | 0.25 |
| | Sodium Carboxyl Betaglucane | 0.25 |
| C | Phenoxyethanol | 0.70 |
| | Methylparaben | 0.20 |
| | Propylparaben | 0.10 |

Procedure:
1. Mix the components of Part A with a homogenizer. Continue homogenizing until a smooth texture is obtained.
2. Mix the components of Part B in a side container.
3. Add the components of Part B to Part A while homogenizing.
4. Continue homogenizing until a uniform smooth texture is obtained.
5. Add the components of Part C to the homogenized components of Part A and B.

What is claimed is:

1. A coated powder material, comprising a powder material having a surface layer that has been
   (a) chemically immobilized with one or more surface-active agents by forming a bond between the one or more surface active agents and the surface of the powder material via a water-soluble salt of a polyvalent metal, and
   (b) coated with an oil,
   wherein
   the one or more surface-active agents are present in an amount of at least about 0.1% by weight, based on the powder material;
   the oil is selected from the group consisting of dimethicone, mineral oil, isostearyl neopentanoate, caprylic/capric triglyceride, and mixtures thereof, and is present in an amount ranging from about 0.1 to 180% by weight, based on the powder material;

the combined weight percentage of the one or more surface-active agents and oil is at least about 4.0% by weight, based on the powder material;
the coated powder material is classified as powdery;
the one or more surface-active agents is selected from one or more of the group consisting of silane, galacturonic acid, glucarolactone, gallic acid, glucoheptanoic acid, 12-hydroxystearic acid, laurylamidobetaine, stearyl amphoacetate, lauryl amphopropionate, stearyl amphopropionate, sodium myristoyl sarosinate, disodium stearoyl glutamate, isostearyl sebacic acid, and combinations thereof;
and
the oil-absorption value of the coated powder material ranges from about 0.10 to about 0.64 gram of oil per gram of the powder material.

2. The coated powder material of claim 1, wherein the one or more surface-active agents are present in an amount ranging from about 1.0 to about 60% by weight, based on the powder material.

3. The coated powder material of claim 2, wherein the one or more surface-active agents are present in an amount ranging from about 3.0 to about 30% by weight, based on the powder material.

4. The coated powder material of claim 1, wherein the oil is present in an amount ranging from about 3.0 to about 120% by weight, based on the powder material.

5. The coated powder material of claim 4, wherein the oil is present in an amount ranging from about 5.0 to about 60% by weight, based on the powder material.

6. The coated powder material of claim 1, wherein the combined weight percentage of the one or more surface-active agents and oil ranges from 4.0 to about 150% by weight, based on the powder material.

7. The coated powder material of claim 6, wherein the combined weight percentage of the one or more surface-active agents and oil ranges from about 8.0 to about 90% by weight, based on the powder material.

8. The coated powder material of claim 1, wherein the powder material is a pigment.

9. The coated powder material of claim 8, wherein the pigment is selected from the group consisting of titanium dioxides, zinc oxides, zirconium dioxides, iron oxides, ultramarine blues, mica, talc, chromium oxides, magnesium silicate, and aluminum silicate.

10. The coated powder material of claim 1, wherein the powder material is in the form of beads.

11. The coated powder material of claim 10, wherein the beads are aluminum/magnesium silicate beads, silica beads, nylon beads, or a combination thereof.

12. The coated powder material of claim 1, wherein the powder material is a material selected from the group consisting of carbon black, cellulose, urethane, styrene, polyolefin, polyethylene, polyamide, acrylate, calcium carbonate, zeolite, fumed silica, metal powder, ceramic powder, and zirconium.

13. A cosmetic product comprising the coated powder material of claim 1.

14. A process for preparing a coated powder material, comprising:
a. introducing a powder material
b. chemically immobilizing the powder material with one or more surface-active agents by bonding the one or more surface-active agents to the surface of the powder material by the addition of a water-soluble salt of a polyvalent metal, the one or more surface-active agents is selected from one or more of the group consisting of silane, galacturonic acid, glucarolactone, gallic acid, glucoheptanoic acid, 12-hydroxystearic acid, laurylamidobetaine, stearyl amphoacetate, lauryl amphopropionate, stearyl amphopropionate, sodium myristoyl sarosinate, disodium stearoyl glutamate, isostearyl sebacic acid, and combinations thereof and
c. coating the chemically immobilized powder material with an oil selected from the group consisting of dimethicone, mineral oil, isostearyl neopentanoate, caprylic/capric triglyceride, and mixtures thereof,
wherein the one or more surface-active agents are present in an amount of about 0.1% or more by weight, based on the powder material; the oil is present in an amount ranging from about 0.1 to 180% by weight, based on the powder material; and the combined weight percentage of the one or more surface-active agents and oil is about 4.0% or more by weigh, based on the powder material and the oil-absorption value of the coated powder material ranges from about 0.10 to 0.64 gram of oil per gram of the powder material.

15. The process of claim 14, wherein the one or more surface-active agents are present in an amount ranging from about 1.0 to about 60% by weight, based on the powder material.

16. The process of claim 15, wherein the one or more surface-active agents are present in an amount ranging from at least about 3.0 to about 30% by weight, based on the powder material.

17. The process of claim 14, wherein the oil is present in an amount ranging from about 3.0 to about 120% by weight, based on the powder material.

18. The process of claim 17, wherein the oil is present in an amount ranging from about 5.0 to about 60% by weight, based on the powder material.

19. The process of claim 14, wherein the combined weight percentage of the one or more surface-active agents and oil ranges from 4.0 to about 150% by weight, based on the powder material.

20. The process of claim 19, wherein the combined weight percentage of the one or more surface-active agents and oil ranges from about 8.0 to about 90% by weight, based on the powder material.

* * * * *